United States Patent
Batdorf

(10) Patent No.: US 7,655,703 B2
(45) Date of Patent: Feb. 2, 2010

(54) METHOD AND APPARATUS FOR METHANOL AND OTHER FUEL PRODUCTION

(75) Inventor: James A. Batdorf, Kennewick, WA (US)

(73) Assignee: Inentec LLC, Richland, WA (US)

( * ) Notice: Subject to any disclaimer, the term of this patent is extended or adjusted under 35 U.S.C. 154(b) by 37 days.

(21) Appl. No.: 11/698,362

(22) Filed: Jan. 26, 2007

(65) Prior Publication Data

US 2008/0182911 A1   Jul. 31, 2008

(51) Int. Cl.
   *C07C 27/00* (2006.01)
(52) U.S. Cl. .................. 518/713; 518/703; 518/704
(58) Field of Classification Search ............. 518/703, 518/704, 713
   See application file for complete search history.

(56) References Cited

U.S. PATENT DOCUMENTS

| | | | |
|---|---|---|---|
| 3,962,300 A * | 6/1976 | Hiller et al. .............. 518/703 |
| 4,772,634 A | 9/1988 | Farooque | |
| 4,790,859 A | 12/1988 | Marumo et al. | |
| 5,310,506 A | 5/1994 | Supp et al. | |
| 5,472,986 A | 12/1995 | van Dijk | |
| 5,523,326 A | 6/1996 | Dandekar et al. | |
| 5,666,891 A | 9/1997 | Titus et al. | |
| 5,756,957 A | 5/1998 | Titus et al. | |
| 5,785,923 A | 7/1998 | Surma et al. | |
| 5,798,497 A | 8/1998 | Titus et al. | |
| 5,811,752 A | 9/1998 | Titus et al. | |
| 5,847,353 A | 12/1998 | Titus et al. | |
| 5,897,686 A | 4/1999 | Golden et al. | |
| 5,908,564 A | 6/1999 | Titus et al. | |
| 6,018,471 A | 1/2000 | Titus et al. | |
| 6,018,542 A | 1/2000 | Berger | |
| 6,037,560 A | 3/2000 | Titus et al. | |
| 6,049,560 A | 4/2000 | Freeman | |
| 6,066,825 A | 5/2000 | Titus et al. | |
| 6,127,645 A | 10/2000 | Titus et al. | |
| 6,160,238 A | 12/2000 | Titus et al. | |
| 6,215,678 B1 | 4/2001 | Titus et al. | |
| 6,371,711 B1 | 4/2002 | Berger | |
| 6,476,084 B2 | 11/2002 | Whitney | |
| 6,570,906 B2 | 5/2003 | Titus | |
| 6,576,210 B2 | 6/2003 | Surma | |
| 6,630,113 B1 | 10/2003 | Surma | |
| 6,737,604 B2 | 5/2004 | Surma et al. | |
| 6,805,107 B2 | 10/2004 | Vinyard | |
| 6,809,121 B1 | 10/2004 | Rytter et al. | |
| 7,037,948 B2 | 5/2006 | Hansen et al. | |
| 7,045,553 B2 | 5/2006 | Hershkowitz | |
| 7,053,128 B2 | 5/2006 | Hershkowitz | |
| 7,067,558 B2 | 6/2006 | Grobys et al. | |

OTHER PUBLICATIONS

U.S. Appl. No. 11/177,152.
U.S. Appl. No. 11/432,826.
Jun Izumi, et al., "Development on High Perfomance Gas Separation Process Using Gas Adsorption," Mitsubishi Heavy Industries, Ltd. Technical Review vol. 39 No. 1 (Feb. 2002).
Dapeng Cao, et al., "Modeling the Selectivity of Activated Carbons for Efficient Separation fo Hydrogen and Carbon Dioxide," Carbon 43 (2005), p. 1364-1370.
Devinder Mahajan, et al., "Integrating Low-Temperature Methanol Synthesis and CO2 Sequestration Technologies: Application to IGCC Plants," Catalysis Today 84 (2003), p. 71-81.

* cited by examiner

*Primary Examiner*—Jafar Parsa
(74) *Attorney, Agent, or Firm*—Douglas E. McKinley, Jr.

(57) ABSTRACT

A method and apparatus for converting organic waste feed streams into usable liquid fuels by adjusting the ratio of carbon dioxide, carbon monoxide, and hydrogen in the effluent gas of a high temperature waste treatment system. A pressure swing adsorption (PSA) unit is used to remove carbon dioxide from the effluent gas of a high temperature waste treatment system, while leaving carbon monoxide and hydrogen, thereby producing a gas stream amenable to the production of methanol and other liquid fuels using commercially available catalytic reactors.

9 Claims, 1 Drawing Sheet

METHOD AND APPARATUS FOR METHANOL AND OTHER FUEL PRODUCTION

TECHNICAL FIELD

This invention relates to the production of methanol and other valuable liquids from organic feedstocks. More specifically, this invention relates to the production of methanol and other alcohols such as ethanol and di-methyl ether from organic waste products.

BACKGROUND OF THE INVENTION

A desire to attain energy independence from foreign producers of petroleum products has recently created tremendous interest in methanol and ethanol as liquid fuels. Typically, this interest is directed at conventional techniques for converting crops such as corn into ethanol and soybeans, rapeseed, and other vegetable oils into bio-diesel fuel. The production of bio-diesel from animal and vegetable oils requires a chemical conversion by reacting the oils with methanol. This in turn creates the need for alternate sources of methanol, preferably renewable sources. One drawback associated with these methods are the costs associated with producing the agricultural feedstocks. Simultaneously with these efforts, the desire to provide a safe and reliable waste disposal method has led to the development of waste treatment systems that generate usable energy as a by product. Examples of such systems are found in the following U.S. patents and pending U.S. patent applications, the entire contents of which are herein incorporated into this disclosure in their entirety by this reference:

U.S. Pat. No. 5,666,891 Arc Plasma-Melter Electro Conversion System for Waste Treatment and Resource Recovery—Issued Sep. 16, 1997, U.S. Pat. No. 5,756,957 Tunable Molten Oxide Pool Assisted Plasma Melter Vitrification System—Issued May 26, 1998, U.S. Pat. No. 5,785,923 Apparatus for Continuous Feed Material Melting—Issued Jul. 28, 1998, U.S. Pat. No. 5,798,497 Tunable, Self-Powered Integrated Arc Plasma-Melter Vitrification System for Waste Treatment and Resource Recovery—Issued Aug. 25, 1998, U.S. Pat. No. 5,811,752 Enhanced Tunable Plasma-Melter Vitrification Systems—Issued Sep. 22, 1998, U.S. Pat. No. 5,847,353 Methods and Apparatus for Low $No_x$ Emissions during the Production of Electricity from Waste Treatment Systems—Issued Dec. 8, 1998, U.S. Pat. No. 5,908,564 Tunable, Self-powered Arc Plasma-melter Electro Conversion System for Waste Treatment and Resource Recovery—Issued Jun. 1, 1999, U.S. Pat. No. 6,018,471 Methods and Apparatus for Treating Waste—Issued Jan. 25, 2000, U.S. Pat. No. 6,037,560 Enhanced Tunable Plasma-Melter Vitrification Systems—Issued Mar. 14, 2000, U.S. Pat. No. 6,215,678 Methods and Apparatus for Treating Waste (Arc Plasma Joule Heated Melter System for Waste Treatment and Resource Recovery)—Issued Apr. 10, 2001, U.S. Pat. No. 6,127,645 Tunable, Self-powered Arc Plasma-melter Electro Conversion System for Waste Treatment and Resource Recovery—Issued Oct. 3, 2000, U.S. Pat. No. 6,160,238 Tunable Molten Oxide Pool Assisted Plasma Melter Vitrification System—Issued Dec. 12, 2000, U.S. Pat. No. 6,066,825 Methods and Apparatus for Low $No_x$ Emissions during the Production of Electricity from Waste Treatment Systems—Issued May 23, 2000, U.S. Pat. No. 6,576,210 Method for Complete Destruction of Carbon in High Temperature Plasma Waste Treatment Systems—Issued Jun. 10, 2003, U.S. Pat. No. 6,630,113 Methods and Apparatus for Treating Waste—Issued Oct. 7, 2003, U.S. Pat. No. 6,018,542 Sealed Electrode Feeding Assembly—Issued Jan. 25, 2000, U.S. Pat. No. 6,049,560 Inductively Heated Side Drain for High Temperature Molten Materials—Issued Oct. 11, 2000, U.S. Pat. No. 6,371,711 Valveless Continuous Atmospherically Isolated Container Feeding Assembly—Issued Apr. 16, 2002, U.S. Pat. No. 6,737,604 Symbiotic Solid Waste Gaseous Waste Conversion System for High Efficiency Electricity Production—Issued May 18, 2004, U.S. Pat. No. 6,570,906 Arc Furnace with DC Arc and AC Joule Heating—Issued May 27, 2003, U.S. Pat. No. 6,805,107 Dual Fuel Source Carburetor Method—Issued Oct. 19, 2004, Ser. No. 11/177,152 filed Jul. 6, 2005 for: Method For Enhancing The Operation Of Electrical Power Plants and Energy Storage Ser. No. 11/432,826 filed May 12, 2006 for Combined Gasification And Vitrification System.

While these waste treatment systems have proven to be effective in converting waste products to useful energy in the form of synthesis gas, there exists a need to convert this synthesis gas into more easily handled liquid fuels and chemical products such as methanol. Unfortunately, the synthesis gas produced by these and similar waste treatment systems does not lend itself to conversion into liquid fuels using known techniques. For example, the inventors of the present invention have discovered that the balance of hydrogen, carbon dioxide, and carbon monoxide that is often produced in these systems is unsuitable for direct conversion to methanol using commercial methods and apparatus. Thus, there exists a need for new methods and apparatus to convert organic waste streams into methanol and other liquid products that overcomes the drawbacks of these prior art systems. The present invention addresses those needs.

SUMMARY OF THE INVENTION

Accordingly, it is an object of the present invention to provide a method and apparatus for converting organic waste feed streams into usable liquid fuels. It is a further object of the present invention to provide a method for adjusting the ratio of carbon dioxide, carbon monoxide, and hydrogen in the effluent gas of a high temperature waste treatment system using commercially available equipment to provide a gaseous mixture that may be catalytically converted into methanol and other liquid fuels using available catalytic reactors. It is a further object of the present invention to operate a pressure swing adsorption (PSA) system to remove carbon dioxide from the effluent gas of a high temperature waste treatment system, while allowing the carbon monoxide and hydrogen to pass through the PSA, thereby producing a gas stream amenable to the production of methanol and other liquid fuels using commercially available catalytic reactors.

These and other objects of the present invention are achieved by providing a method for converting an organic waste stream into methanol and other liquid products. As used herein, "organic waste stream" includes, but is not limited to, biomass; such as agricultural byproducts, crop residues, and byproducts from forestry and paper making operations; municipal solid waste, auto shredder residue, waste tires, waste oils, and the like. Generally, the method of the present invention begins by heating waste materials in the presence of oxygen and steam to produce a synthesis gas having a stoichiometric number of less than 1. As used herein, "stoichiometric number" means the ratio of the mole percentage of $H_2$, CO, and $CO_2$ in a gas stream as calculated by the following equation:

$$(H_2-CO_2)/(CO+CO_2).$$

A sufficient amount of $CO_2$ is then removed from the synthesis gas to adjust the stoichiometric number of the synthesis gas to over 1. The synthesis gas is then exposed to a catalyst at sufficient heat and pressure to produce an organic liquid.

The present invention may also include the step of cleaning the synthesis gas to remove contaminants. Typical contaminants include, but are not limited to, carbon and other particulates, HCl, $H_2S$.

The organic liquid formed by the present invention is preferably methanol, but may be a variety of liquids commonly used as chemical products, or fuel sources, including but not limited to methanol, ethanol, propanol, butanol, di-methyl ether, Fischer Tropsch liquids, and combinations thereof.

Preferably, the step of removing a sufficient amount of $CO_2$ to adjust the stoichiometric number of the synthesis gas to over 1 is accomplished by the use of a pressure swing adsorber (PSA). The design of PSA units dates back to at least 1966, when PSA units were first utilized for the recovery of hydrogen from a wide range of gas streams. A typical PSA consists of a chamber with an inlet and an outlet. In a typical operation of a PSA, a gas is fed into the PSA at the inlet, and a hydrogen product is removed at the outlet. Inside the chamber, gaseous components of the gas streams are adsorbed on commercial adsorbents such as molecular sieves, silica gel, or activated carbon. The specific adsorption is effected by several factors, among which volatility and polarity tend to be most important. As process conditions approach the dew point of a component, a less volatile component is adsorbed from the gas phase. Adsorption may further be aided by electrostatic forces. A strong preference by polar adsorbents is shown for the polar or polarizable molecules. These molecules are attracted by the adsorptive forces of the positively charged cations contained in the crystal lattice of the adsorbent. Highly volatile compounds with little polarity, such as hydrogen and helium, are essentially non-adsorbable compared with other molecules. The PSA thus tends to perform a separation and a chromatographic fashion, with the heavier gases adsorbed toward the inlet of the vessel and the lighter gas is adsorbed toward the outlet of the vessel. As a result, carbon dioxide is typically adsorbed more readily than carbon monoxide, which in turn is more readily adsorbed than hydrogen.

Typically, once the adsorbent is loaded with an impurity, it is regenerated by reducing the adsorbent pressure. At lower pressures the adsorbent's capacity is reduced, and impurities are desorbed. After the adsorbent is regenerated, it must be repressurized to be ready for a new adsorption step. In the classical operation of the PSA, it is run until the adsorbent is loaded with carbon monoxide. Since PSA units are run to produce hydrogen, at the point that carbon monoxide begins to appear in the hydrogen product, the regeneration step is performed.

The operation of the PSA in the present invention differs from the classical operation of a PSA, because in the present invention the PSA continues to operate even though carbon monoxide is present in the hydrogen gas stream. In the present invention, the regeneration step is only performed once carbon dioxide begins to appear in hydrogen gas stream. Thus, the present invention preferably performs the step of removing a sufficient amount of $CO_2$ to adjust the stoichiometric number of the synthesis gas to over 1 by first introducing a flow of synthesis gas into a pressure swing adsorber. The flow of synthesis gas is then maintained through the pressure swing adsorber until the capacity of the pressure swing adsorber to adsorb additional $H_2$ and CO is substantially exhausted and the capacity of the pressure swing adsorber to adsorb additional $CO_2$ is not substantially exhausted. In this manner, the PSA is used to produce a mixture of $H_2$ and CO, rather than pure $H_2$, as is the case in the typical operation of the PSA unit. Preferably, the synthesis gas is introduced into the pressure swing adsorber at a pressure of between about 5 psia and about 200 psia.

The resultant synthesis gas having a stoichiometric number greater than 1 is then exposed to the catalyst at pressures between about 10 bar and about 100 bar, and temperatures between about 200 and 400 C to produce a fuel. The catalyst is preferably selected as a low temperature methanol synthesis catalyst. Suitable catalysts thus include, but not limited to, copper oxide, zinc oxide, and alumina; dimethyl ether catalysts, dehydration catalysts, metals, metal oxides, and combinations thereof.

It is preferred that the method of the present invention include the step of removing mercury from the synthesis gas. It is also preferred that the method of the present invention include the step of removing organic contaminants from the synthesis gas. The step of removing organic contaminants from the synthesis gas may also be performed with the use of a second pressure swing adsorber.

As used herein, "organic contaminants" includes, but are not limited to, benzene, naphthalene, toluene, oils, waxes, and combinations thereof.

BRIEF DESCRIPTION OF THE DRAWINGS

The following detailed description of the embodiments of the invention will be more readily understood when taken in conjunction with the following drawing, wherein.

DETAILED DESCRIPTION OF THE PREFERRED EMBODIMENTS

Figure 1:
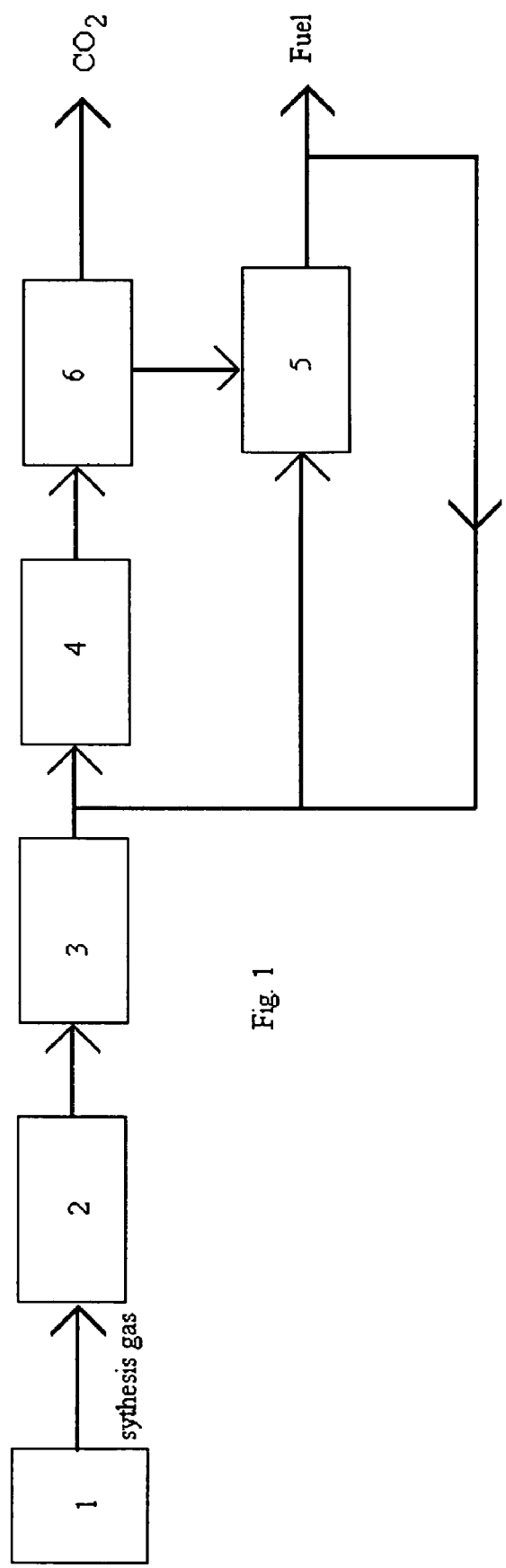
FIG. 1 is a schematic illustration of the method and apparatus of the present invention.

For the purposes of promoting an understanding of the principles of the invention, reference will now be made to the embodiments illustrated in the drawings and specific language will be used to describe the same. It will nevertheless be understood that no limitations of the inventive scope is thereby intended, as the scope of this invention should be evaluated with reference to the claims appended hereto. Alterations and further modifications in the illustrated devices, and such further applications of the principles of the invention as illustrated herein are contemplated as would normally occur to one skilled in the art to which the invention relates.

FIG. 1 illustrates a preferred embodiment of the present invention. As shown in FIG. 1, synthesis gas consisting primarily of carbon dioxide, carbon monoxide, and hydrogen from a high temperature waste treatment system 1 enters guard bed 2 which removes trace organics in the synthesis gas from the waste treatment system 1. From guard bed 2, synthesis gas enters mercury removal unit 3 which removes any mercury from the syntheses gas. A portion of the synthesis gas is then directed into water gas shift reactor 4, while another portion is directed into catalytic reactor 5 for producing liquid fuels. Within water gas shift reactor 4 carbon monoxide in the synthesis gas is combined with water, typically in the form of steam, to produce carbon dioxide and hydrogen. The resultant hydrogen rich synthesis gas is then fed into PSA 6.

PSA 6 removes a sufficient amount of $CO_2$ so that when the hydrogen rich synthesis gas from PSA 6 is combined with synthesis gas from the mercury removal unit 3, the stoichiometric number of the combined gas is adjusted such that it is over 1. This is accomplished by maintaining the flow of synthesis gas through the PSA 6 until the capacity of PSA 6 to adsorb additional $H_2$ and CO is substantially exhausted and the capacity of PSA 6 to adsorb additional $CO_2$ is not substantially exhausted. In this manner, PSA 6 is used to produce a mixture of $H_2$ and CO, which, when combined with synthesis gas that has not been enriched in hydrogen and carbon monoxide content to just a stoichiometric number of the combined gas to greater than 1. The combined gas is then looped through a catalytic reactor vessel 5 to produce a fuel gas such as methanol or dimethyl ether.

While the invention has been illustrated and described in detail in the drawings and foregoing description, the same is to be considered as illustrative and not restrictive in character. Only certain embodiments have been shown and described, and all changes, equivalents, and modifications that come within the spirit of the invention described herein are desired to be protected. Any experiments, experimental examples, or experimental results provided herein are intended to be illustrative of the present invention and should not be considered limiting or restrictive with regard to the invention scope. Further, any theory, mechanism of operation, proof, or finding stated herein is meant to further enhance understanding of the present invention and is not intended to limit the present invention in any way to such theory, mechanism of operation, proof, or finding.

Thus, the specifics of this description and the attached drawings should not be interpreted to limit the scope of this invention to the specifics thereof. Rather, the scope of this invention should be evaluated with reference to the claims appended hereto. In reading the claims it is intended that when words such as "a", "an", "at least one", and "at least a portion" are used there is no intention to limit the claims to only one item unless specifically stated to the contrary in the claims. Further, when the language "at least a portion" and/or "a portion" is used, the claims may include a portion and/or the entire items unless specifically stated to the contrary. Likewise, where the term "input" or "output" is used in connection with an electric device or fluid processing unit, it should be understood to comprehend singular or plural and one or more signal channels or fluid lines as appropriate in the context. Finally, all publications, patents, and patent applications cited in this specification are herein incorporated by reference to the extent not inconsistent with the present disclosure as if each were specifically and individually indicated to be incorporated by reference and set forth in its entirety herein.

I claim:

1. A method for converting an organic waste stream into an organic liquid comprising the steps of:
    a. heating the waste in the presence of oxygen and steam to produce a synthesis gas having a stoichiometric number of less than 1,
    b. removing a sufficient amount of $CO_2$ to adjust the stoichiometric number of the synthesis gas to over 1 by introducing a flow of the synthesis gas through a pressure swing adsorber,
    c. maintaining the flow of synthesis gas through the pressure swing adsorber until the capacity of the pressure swing adsorber to adsorb additional $H_2$ and CO is substantially exhausted, and the capacity of the pressure swing adsorber to adsorb additional $CO_2$ is not substantially exhausted, and
    d. exposing the synthesis gas to a catalyst at sufficient heat and pressure to produce an organic liquid.

2. The method of claim 1 further comprising the step of cleaning the synthesis gas to remove at least one contaminant selected from the group particulate, HCl, $H_2S$.

3. The method of claim 1 wherein the organic liquid is selected from methanol, ethanol, propanol, butanol, di-methyl ether, Fischer Tropsch liquids, and combinations thereof.

4. The method of claim 1 wherein the synthesis gas is exposed to the catalyst at pressures between about 10 bar and about 100 bar, and temperatures between about 200 and 400 C.

5. The method of claim 1 wherein the synthesis gas in the pressure swing adsorber is at a pressure of from about 5 psia and 200 psia.

6. The method of claim 1 wherein the catalyst is selected as low temperature methanol synthesis catalysts, including but not limited to, copper oxide, zinc oxide, and alumina; dimethyl ether catalysts, dehydration catalysts, metals, metal oxides, and combinations thereof.

7. The method of claim 1 further comprising the step of removing mercury from the synthesis gas.

8. The method of claim 1 further comprising the step of removing organic contaminants from the synthesis gas.

9. The method of claim 1 further comprising the step of removing organic contaminants from the synthesis gas in the pressure swing adsorber.

* * * * *